US009265516B2

(12) United States Patent
Casey et al.

(10) Patent No.: US 9,265,516 B2
(45) Date of Patent: Feb. 23, 2016

(54) BLADE RETENTION MECHANISM FOR SURGICAL INSTRUMENT (71) Applicant: GYRUS ACMI, INC., Southborough, MA (US)

(72) Inventors: Jay A. Casey, Memphis, TN (US); Kevin C. Edwards, Olive Branch, MS (US); Tomas Matusaitis, Chicago, IL (US)

(73) Assignee: GYRUS ACMI, Inc., Southborough, MA (US)

( * ) Notice: Subject to any disclaimer, the term of this patent is extended or adjusted under 35 U.S.C. 154(b) by 272 days.

(21) Appl. No.: 13/835,517

(22) Filed: Mar. 15, 2013

(65) Prior Publication Data

US 2014/0005700 A1 Jan. 2, 2014

Related U.S. Application Data (60) Provisional application No. 61/666,131, filed on Jun. 29, 2012, provisional application No. 61/697,082, filed on Sep. 5, 2012.

(51) Int. Cl.
*B23B 31/107* (2006.01)
*A61B 17/32* (2006.01)
(Continued)

(52) U.S. Cl.
CPC ................. *A61B 17/32* (2013.01); *A61B 17/00* (2013.01); *B23B 31/1071* (2013.01);
(Continued)

(58) Field of Classification Search
CPC ........... B23B 31/1071; B23B 2231/44; A61B 17/32002; A61B 2017/0046; A61B 2017/00477; Y10T 279/17717

USPC ................................. 279/71, 72, 81; 433/128
See application file for complete search history.

(56) References Cited

U.S. PATENT DOCUMENTS 3,822,951 A   7/1974 Bornzin
4,014,099 A * 3/1977 Bailey ........................... 433/128
(Continued)

FOREIGN PATENT DOCUMENTS

CN          1736346 A    2/2006
CN       202105229 U    10/2011
(Continued)

OTHER PUBLICATIONS

Japanese Office Action for Japanese application No. 2014-525206 dated Jul. 22, 2014.
(Continued)

*Primary Examiner* — Eric A Gates
(74) *Attorney, Agent, or Firm* — The Dobrusin Law Firm, P.C.

(57) ABSTRACT

A surgical apparatus which includes a handpiece having a passage. The retention assembly includes a pair of radially movable buttons, aligned in axially extending passages in communication with the passage and can engage with and cause rotational movement of a collet member assembly rotatably supported in the passage. The collet assembly includes rolling lock members which can be moved by the collet member from a lock position, in which the lock members are forced by the wall of the passage to extend inwardly of the collet member and an unlocked position, in which the lock members are aligned with a recess in the wall of the passage and are not forced to extend inwardly of the collet member. The surgical apparatus may find particular use with irrigation fluid, suction, and powering of a surgical tool. The passage may include a cutting blade retention assembly integrated in the passage.

14 Claims, 11 Drawing Sheets

(51) Int. Cl.
  *B23B 31/20* (2006.01)
  *A61B 17/00* (2006.01)
  *A61B 17/29* (2006.01)
  *A61B 17/3207* (2006.01)

(52) U.S. Cl.
  CPC .......... *B23B 31/201* (2013.01); *A61B 17/2909* (2013.01); *A61B 17/32002* (2013.01); *A61B 17/320783* (2013.01); *A61B 2017/0046* (2013.01); *A61B 2017/00477* (2013.01); *Y10T 29/49826* (2015.01); *Y10T 279/17316* (2015.01); *Y10T 279/17717* (2015.01)

(56) References Cited

U.S. PATENT DOCUMENTS

| | | | | |
|---|---|---|---|---|
| 4,690,641 | A * | 9/1987 | Luiset et al. | 433/129 |
| 4,697,894 | A | 10/1987 | Takamura et al. | |
| 4,708,548 | A | 11/1987 | Taylor et al. | |
| 4,820,154 | A * | 4/1989 | Romhild et al. | 433/128 |
| 4,874,314 | A * | 10/1989 | Fleer et al. | 433/129 |
| 5,028,181 | A * | 7/1991 | Jenkins et al. | 409/215 |
| 5,037,299 | A * | 8/1991 | Nakanishi | 433/128 |
| 5,390,571 | A * | 2/1995 | Fox et al. | 81/177.85 |
| 5,492,527 | A | 2/1996 | Glowa | |
| 5,569,256 | A | 10/1996 | Vaughn et al. | |
| 5,578,052 | A | 11/1996 | Koros et al. | |
| 5,584,689 | A * | 12/1996 | Loge | 433/128 |
| 5,704,786 | A * | 1/1998 | Quinn | 433/128 |
| 6,082,516 | A * | 7/2000 | Willer | 192/223.2 |
| 6,129,392 | A | 10/2000 | Dittrich et al. | |
| 6,139,214 | A | 10/2000 | Zirps | |
| 6,270,087 | B1 | 8/2001 | Mickel | |
| 6,675,911 | B2 | 1/2004 | Driessen | |
| 6,688,611 | B2 | 2/2004 | Gifford et al. | |
| 7,040,023 | B2 * | 5/2006 | Nemazi et al. | 30/392 |
| 7,226,460 | B2 | 6/2007 | Gibson et al. | |
| 7,237,990 | B2 | 7/2007 | Deng | |
| 7,591,829 | B2 | 9/2009 | Gibson et al. | |
| 7,799,044 | B2 | 9/2010 | Johnston et al. | |
| 8,075,311 | B2 * | 12/2011 | Pernot | 433/128 |
| 2003/0066667 | A1 | 4/2003 | Zhang | |
| 2008/0182226 | A1 * | 7/2008 | Pernot | 433/146 |
| 2009/0033042 | A1 * | 2/2009 | Rinner | 279/72 |
| 2011/0022172 | A1 | 1/2011 | Gonzales et al. | |

FOREIGN PATENT DOCUMENTS

| | | |
|---|---|---|
| DE | 3541855 A1 | 6/1986 |
| DE | 19514098 A1 | 10/1996 |
| GB | 2131915 A | 6/1984 |
| JP | S49-49046 | 5/1974 |
| JP | S61-99118 A | 5/1986 |
| JP | H06-343639 A | 12/1994 |
| JP | 2013-545532 A | 12/2013 |
| WO | 2008-099281 A2 | 8/2008 |

OTHER PUBLICATIONS

International Search Report and Written Opinion dated May 27, 2013; PCT/US2013/031460.
Written Opinion and Search Report for PCT/US2013/031460 mailed May 27, 2013.
Chinese Office Action for Chinese Application No. 201380002686.1 dated Aug. 5, 2015.

* cited by examiner

BLADE RETENTION MECHANISM FOR SURGICAL INSTRUMENT

FIELD

The present disclosure relates to a powered surgical apparatus and a method of using the powered surgical apparatus. In particular, the present disclosure relates to such a powered surgical apparatus usable with a surgical tool, such as a cutting blade assembly, to shave, cut and/or remove tissue, bone and/or any other bodily material, the surgical apparatus including a blade retention mechanism that is capable of quickly and effectively coupling and uncoupling the surgical tool.

BACKGROUND

Surgical apparatuses are generally known to be powered to enhance shaving, cutting and/or removal of tissue, bone and/or other bodily material. Powered surgical apparatuses generally include a coupling mechanism for selectively coupling and uncoupling a tool or instrument, including but not limited to an instrument for shaving or cutting tissue or bone, such as a rotating blade, for example. The rotating blade instrument can be coupled or connected to a handpiece to be held by an operator, such as a surgeon. The surgeon, by holding the handpiece, can thereby manipulate the rotating blade to shave or cut desired tissue, bone and/or other bodily material. Further, when coupling or uncoupling the rotating blade instrument or other tool with the handpiece, the operator may also couple other connections such as fluid supply or suction.

Generally understood examples of a surgical apparatus including a coupling and uncoupling device are disclosed in U.S. Pat. No. 5,492,527 (hereinafter "the 527 patent"); U.S. Pat. No. 7,799,044 (hereinafter "the 044 patent") and U.S. Pat. No. 7,591,829 (hereinafter the 829 patent"), the entire disclosures of which are incorporated herein by reference. The 527 patent specifically discloses a surgical shaver for use in endoscopic surgical procedures that drives an elongated rotatable surgical instrument and aspirates material from a surgical work site as shown in FIGS. 1-5 and 14 of the 527 patent. The surgical shaver includes a handpiece with a distal end including a collet assembly for attaching and detaching tools to the body of the handpiece 10 including a tool having an elongated rotatable inner blade and an elongated outer blade. The collet assembly of the 527 patent is manually rotatable to enable rotation of the cutting window.

The 044 patent discloses a powered surgical apparatus including a cutting blade assembly connectable with a handle and having a manually actuable input device providing at least one signal relevant to at least one operation of the system and a controller that received the at least one input signal and provide an output signal to perform at least one operation of the system. The 829 patent discloses a surgical implement for use with a hand-piece of a surgical instrument for performing a surgical treatment.

Although conventional surgical instruments are generally understood and considered generally reliable, these prior art assemblies are still relatively complex in construction and operation. An added disadvantage is that the known designs are generally structurally complicated and result in relatively higher manufacturing costs for the medical instrument.

Despite the long-known solutions, there remains a significant need to provide an improved surgical apparatus capable of providing improved performance and gains in efficiency, performance, cost and packaging of the surgical apparatus and associated instruments and tools. Despite the long-known solutions, there remains a significant need to provide an improved surgical apparatus that can overcome the problems of the known art.

SUMMARY

In one exemplary embodiment there is disclosed a surgical apparatus including a main body for quickly coupling and uncoupling a surgical tool such as a cutting blade tool. In one exemplary embodiment the main body includes a first generally cylindrical passage having a proximal end and a distal end, a second radially extending passage extending from the first generally cylindrical passage, and a channel further defining the first generally cylindrical passage. In one exemplary embodiment the surgical apparatus further includes a collet member supported for rotational movement in the first generally cylindrical passage of the main body, the collet member including a first inner surface and a passage having a first length for cooperation with a lock member having a second length aligned in the passage of the collet member, the lock member extending radially inward beyond the inner surface of the collet member. In the one exemplary embodiment, the surgical apparatus further includes a biasing device for biasing the collet member in a first rotational direction within the first generally cylindrical passage of the main body and wherein the second length of the lock member is greater than the first length of the passage of the collet member such that the collet member limits the movement of the lock member and retains the lock member within the first generally cylindrical passage of the main body. In the one exemplary embodiment, the surgical apparatus further includes an actuator that is radially movable in the second radially extending passage of the main body and the actuator includes a second surface for engaging the first surface of the collet member wherein radially inward movement of the actuator rotates the collet member within the first generally cylindrical passage against the force of the biasing member and moves the lock member from a first locked position to a second unlocked position wherein the lock member can move radially outward to be at least partially located in the channel of the main body.

In another exemplary embodiment the surgical apparatus further includes a cover member aligned with the distal end of the collet member for covering the collet member and at least a portion of the distal end of the first generally cylindrical passage of the main body. In yet a further exemplary embodiment, the surgical apparatus wherein the disc-shaped cover member includes first and second tabs each extending in a direction aligned with an axis of the first generally cylindrical passage of the main body and wherein the first and second tabs are oppositely spaced.

In another exemplary embodiment, there is disclosed a powered surgical apparatus for powering a surgical tool such as a cutting blade. The surgical apparatus includes a handpiece and a cutting blade retention assembly integrated in passage in a distal end of the handpiece. The retention assembly includes an aligned, pair of movable buttons, aligned in radially extending passages in communication with the passage in the distal end of the handpiece, the movable buttons can engage with and cause rotational movement of a collet member assembly rotatably supported in the passage in the distal end of the handpiece. The collet assembly includes a plurality of rolling lock members which can be moved by the collet member from a first or locked position, in which the lock members are forced by the wall of the passage to extend inwardly of the collet member to engage an annular groove of the surgical tool, and a second or unlocked position, in which the lock members are aligned with a recess in the wall of the passage and are not forced to extend inwardly of the collet member.

DETAILED DESCRIPTION

This application claims priority from U.S. Provisional Applications 61/666,131 filed Jun. 29, 2012 and 61/697,082 filed Sep. 5, 2012 both incorporated herein by reference in their entirety.

Referring to all of the Figures in general, there are disclosed exemplary embodiments of a powered surgical apparatus 10 according to the present disclosure. The disclosed surgical apparatus 10 is particularly useful for performing surgery, including but not limited to surgery on a human or other animal, and may be used in any known or appropriate surgical procedure. The surgical apparatus 10 can be used to cut, shave and/or remove tissue, bone and/or any other bodily material in a variety of surgical procedures, such as general ear, nose and throat (hereinafter "ENT"), head and neck, and otoneurological procedures, for example, and in particular as a sinus debrider. However, the surgical apparatus 10 can be used in other surgical procedures. More specifically, the invention can be used in sinus procedures, such as ethmoidectomy/sphenoethmoidectomy, polypectomy, septoplasty, antrostomy, endoscopic DCR, frontal sinus drill-out, frontal sinus trephination and irrigation, septal spurs removal, and trans-spehnoidal procedures, for example. The surgical apparatus 10 can be used in nasopharyngeal/laryngeal procedures, such as adenoidectomy, laryngeal lesion de-bulking, laryngeal polypectomy, tracheal procedures, and tonsillectomy, for example. The invention can also be used in head & neck procedures, such as soft tissue shaving, rhinoplasty (narrowing the bony vault and revision of the bony pyramid), removal of fatty (adipose) tissue (lipodebridement) in the maxillary and mandibular regions of the face, and acoustic neuroma removal, for example. The surgical apparatus 10 can also be used in otology procedures, such as mastoidectomy, and mastoidotomy, for example.

The above list of surgical operations and procedures is not intended to be exhaustive, and the surgical apparatus 10 in accordance with the present disclosure is intended to be used in any other applicable currently known or later developed surgical operation and procedure. In fact, the surgical apparatus 10 in accordance with the present disclosure is not only intended to be used in surgical operations and procedures for humans, but can also be used in applicable surgical operations and procedures for other animals and other organic matter. However, even though the surgical apparatus 10 is intended to be usable in a variety of other applications, for convenience of explanation it is described below in the context of human surgery, such as ENT surgery. In this context, the surgical apparatus 10 and methods in accordance with the invention can be provided to comply with, but may not necessarily need to be provided to comply with, standards for surgical instruments, such as the following current voluntary standards: UL 2601-1: Medical Electrical Equipment, Part 1: General Requirements for Safety Australian Deviations, CSA 22.2 No. 601: Canadian Standards, IEC 601-1-1 (EN 60601-1): Medical Electrical Equipment, Part 1: General Requirements for Safety, IEC 601-1-2 (EN 60601-1-2) Medical Safety Equipment, Part 2: Particular Requirements for Safety, IEC 601-1-4 (EN 60601-1-2) Medical Electrical Equipment, Part 1: General Requirements for Safety 4. Collateral Standard: Programmable Electrical Medical Systems, IEC 61000-4-2: Electromagnetic Compatibility (EMC)-Part 4: Testing and Measurement Techniques-Section 2: Electrostatic Discharge Immunity Test, IEC 61000-4-3: Electromagnetic Compatibility (EMC)-Part 4: Testing and Measurement Techniques-Section 3: Radiated, Radio Frequency, Electromagnetic Field Immunity Test, IEC 61000-4-4: Electromagnetic Compatibility (EMC)-Part 4: Testing and Measurement Techniques-Section 4: Electrical Fast Transient/Burst Immunity, IEC 61000-4-5: Electromagnetic Compatibility (EMC)-Part 4: Testing and Measurement Techniques-Section 5: Surge, IEC 529: Installation Protective Equipment, ISO 10993-1: Biological Evaluation of Medical Devices, and EN 55011 Limits and Methods of Measurement of Electromagnetic Disturbance Characteristics of Industrial, Scientific, and Medical (ISM) Radio-Frequency Equipment, Class B, for example.

The surgical apparatus 10 and methods in accordance with the disclosure can also be provided to comply with other current standards and/or any later developed standards. The surgical apparatus 10 and its components (including in particular the handpiece or handle 30, the handle assembly, the surgical tool 20 including its cutting blade assembly 21 and the powered apparatus assembly) are generally understood as explained in U.S. Pat. No. 7,799,044, issued Sep. 21, 2010, entitled Powered Surgical Apparatus, Method Of Manufacturing Powered Surgical Apparatus, And Method Of Using Powered Surgical Apparatus, to Johnston et al., the entire contents of which are incorporated herein by reference for all purposes.

Figure 1:
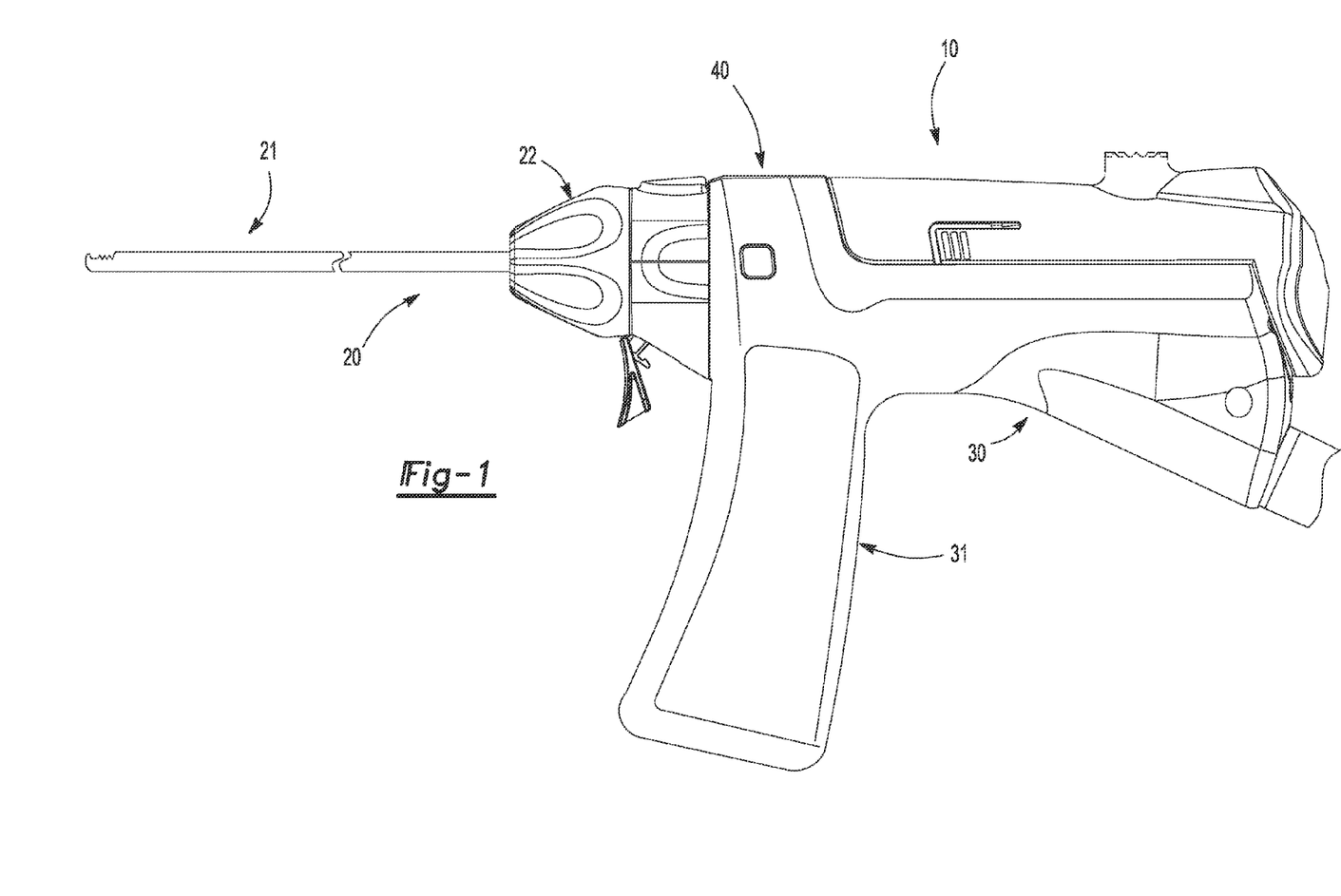
FIG. 1 is a side view of an alternate embodiment of a surgical device and blade retention mechanism including a pistol grip.
Figures 2, 3:
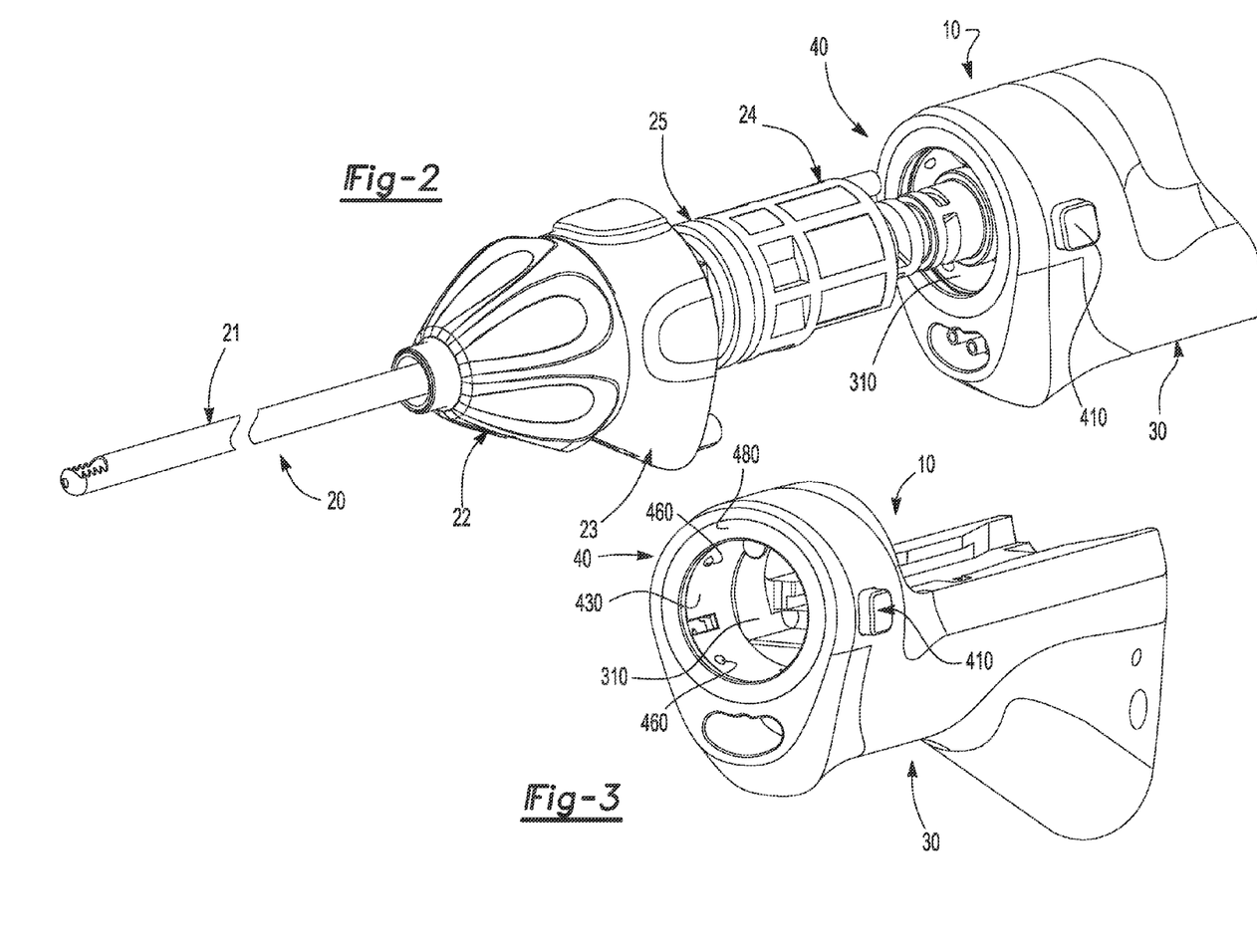
FIG. 2 is a general perspective view of the surgical device and blade retention mechanism showing the cutting blade detached.
FIG. 3 is a partial, perspective view of the handpiece of the surgical device and blade retention mechanism.

Referring now in particular to FIGS. 1-3, the surgical apparatus 10 is powered by a motor and can include a tube set (including a source of irrigation fluid and a source of suction, as best shown in FIG. 3) and an electrical connection for powering the motor to operate the surgical tool 20 including a cutting blade 21. The surgical apparatus 10 includes a handpiece 30 and a surgical tool or blade retention assembly 40 integrated in a distal end 33 of the handpiece 30. The retention assembly 40 is operable for selectively coupling and uncoupling the surgical tool 20 with the handpiece 30. The retention assembly 40 is manually and relatively highly-efficiently operated for more quickly and easily coupling and uncoupling the surgical tool 20 and the handpiece 30. The handpiece 30 is preferably a pencil-type design so the surgical apparatus 10 can be used by an operator and held in a manner similar to how a pencil is held. In one alternate exemplary embodiment as shown in FIG. 2, the handpiece 30 includes a pistol grip 31 extending in a substantially radial direction proximal the distal end 33 of the handpiece 30 so that an operator may use a pistol-type grip when using the surgical apparatus 10.

The surgical tool 20 includes a first collar member 22 from which the cutting blade assembly 21 extends in one axial direction and from which a second collar member 23 extends in an opposite axial direction. The surgical tool 20 and its components all are generally aligned along a longitudinal axis of the surgical tool 20. The surgical tool 20 further includes an extension member 24 having a generally cylindrical outer shape surface which can include therein an annular groove 25. The outer shape of the extension member 24 is preferably matched so it can be received in the passage in the distal end of the handpiece 30 as more fully described below. The surgical tool 20 is preferably secured to the handpiece 30 by inserting extension member 24 in the passage in the distal end of the handpiece 30 in a single action which also couples the working components of the surgical tool 20 with the supply sources of the handpiece 30. Once the extension member 24 is inserted in the passage in the distal end 33 of the handpiece 30, the retention mechanism 40 can be operative to engage the annular groove 25 of the extension member 24 of the surgical tool 20 to retain or secure the surgical tool 20 to the handpiece 30. Particular reference to FIG. 2 shows the insertion of the extension member 24 of the surgical tool 20 in the passage 310 and the incorporation of the retention mechanism 40 in the distal end 33 of the handpiece 30.

Figure 4:
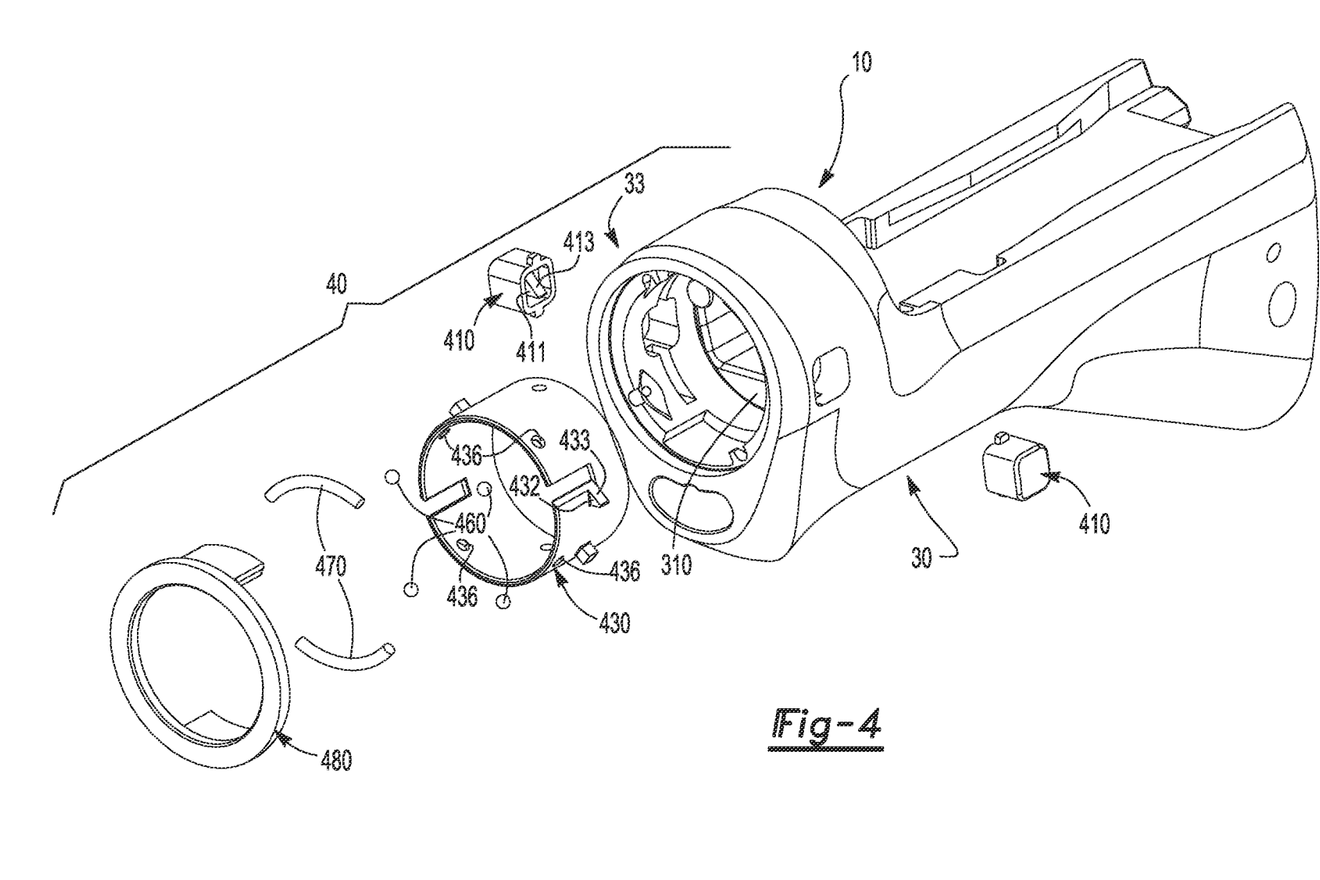
FIG. 4 is an exploded, perspective view of the handpiece of the surgical device and blade retention mechanism.
Figure 5:
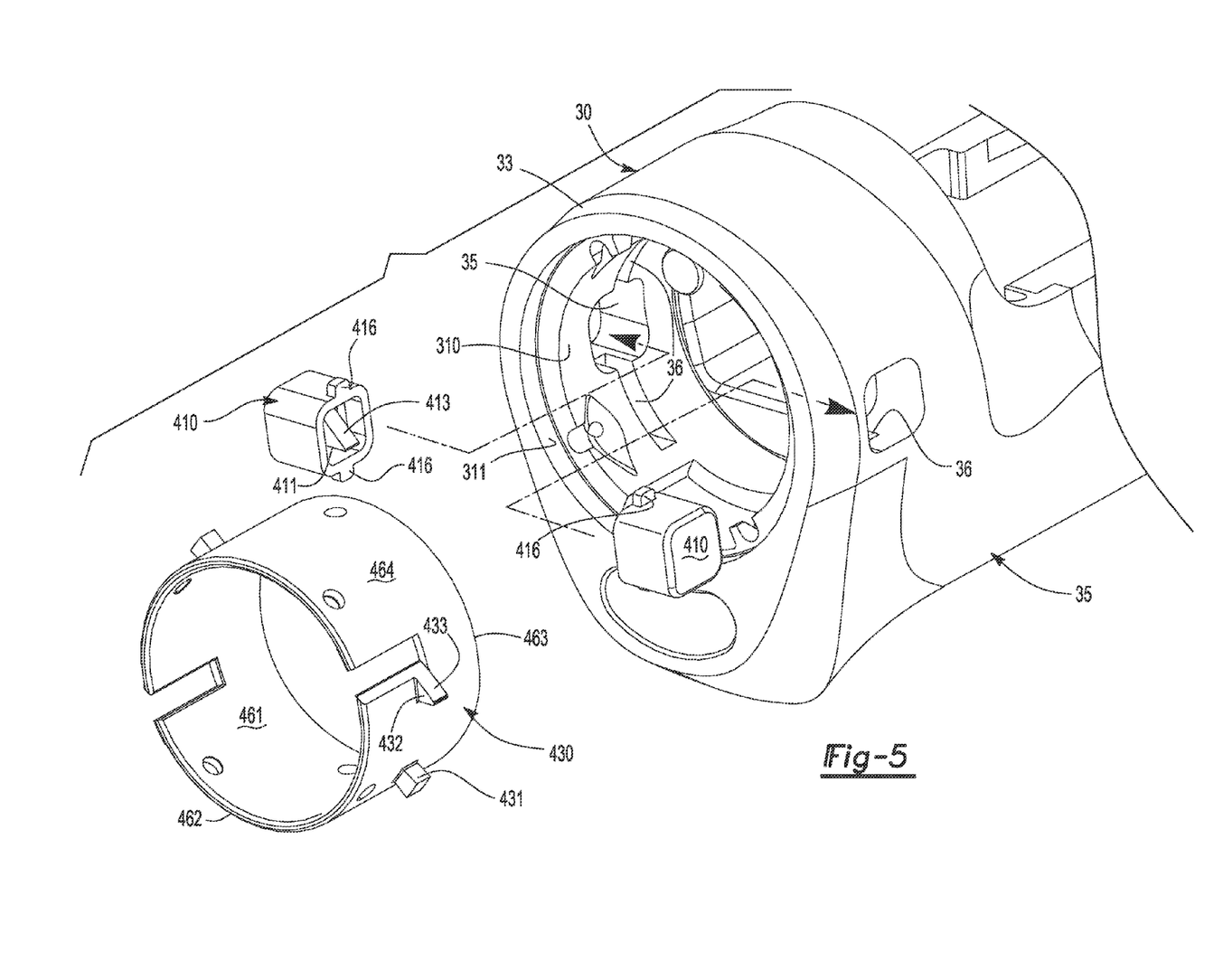
FIG. 5 is a partial, exploded, perspective view of the handpiece of the surgical device and blade retention mechanism.

Referring now in particular to FIGS. 4-5, additional aspects of the retention mechanism 40 and the distal end 33 of the handpiece 30 are detailed. The distal end 33 can include a generally cylindrical, axially extending passage 310 including a first recess step 311. The retention assembly 40 can also include a collet assembly 50 and an aligned pair of axially movable buttons 410 aligned generally with each other and each in a radially extending passage 35 in the distal end 33 of the handpiece 30. It should be noted that it is significant that the collet assembly 50 can be nearly completely internally disposed in the handpiece 30. The only portion of the retention mechanism 40 and collet assembly 50 that is external to the handpiece 30 are the buttons 410. All other aspects of the retention mechanism 40 and collet assembly 50 are internal to the handpiece 30. Each button 410 can project from the handpiece 30 for operation by an operator.

Figure 6:
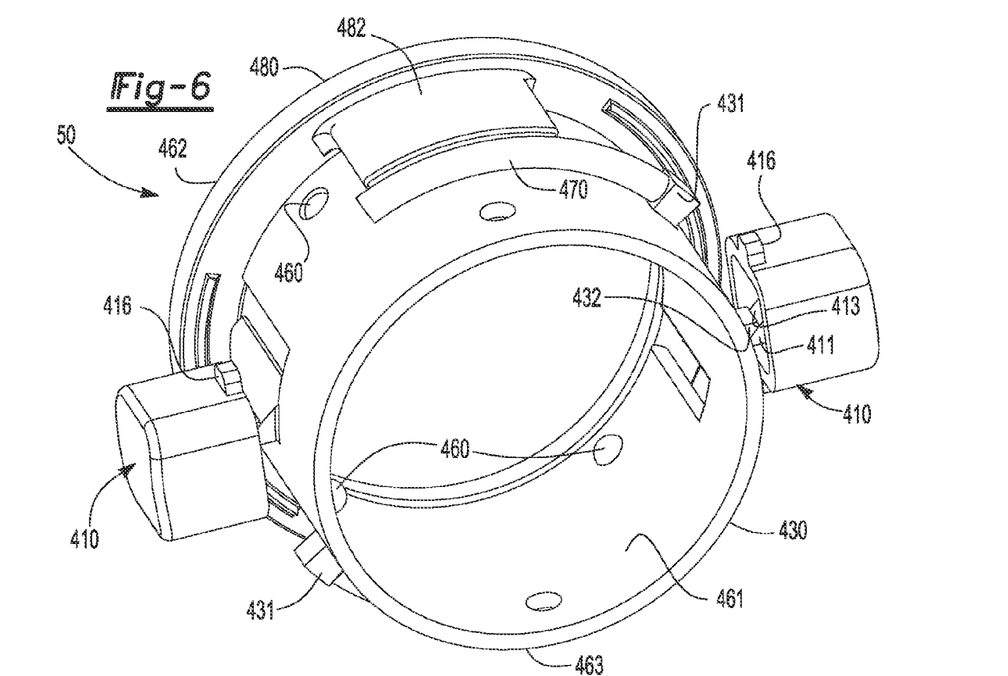
FIG. 6 is a perspective view of the collect member assembly of the handpiece of the blade retention mechanism of the surgical device in a first or locked position.

While each button 410 has a generally five-sided, general trapezoidal shape such that there is a single open side or missing wall, but there are a right side button 410 and a left side button 410. Each of the right side button 410 and the left side button 410 include angled side walls where the top of the angled side walls is closer to the distal end 33 of the handpiece 30, as best shown in FIGS. 2 and 6. On the inner side of the wall opposite the open or missing wall of the button 410, there is an extension member 411 extending toward the open or missing wall and including an inclined or ramped surface 413. Each radial passage 35 can be generally shaped to match the outer surface shape of the respective button 410 which is axially movable in the radial passage 35. Each radial passage 35 is in communication with the generally cylindrical, axially extending passage 310 in the distal end 33 of the handpiece 30.

Each button 410 also includes a pair of outwardly aligned extension members 416 for retaining the button 410 within the radial passage 35 and to prevent rotation of the button 410 within the radial passage 35. Each radial passage 35 includes an upper and a lower partial annular groove 36 extending there-from but does not extend axially to the outer surface of the distal end 33 of the handpiece 30 such that each partial annular groove 36 is a stop for limiting how far the button 410 can move axially outward in the radial passage 35 and to prevent rotation of the button 410 within the radial passage 35. Accordingly, the buttons 410 can only be inserted in a respective radial passage 35 via the generally cylindrical, axially extending passage 310. The buttons 410 are not identical because they are designed to be used on a specific side of the device. Accordingly, there is a right side button 410 and a left side button 410 that are installed in the respective, radial passage 35 aligned one hundred eighty degrees (180) from each other. The ramped surface 413 of each button 410 is generally aligned substantially parallel with the other. Each button 410 is biased radially outward in each radial passage 35 until each extension member 416 engages a respective end of each groove 36.

The retention mechanism 40 can also include the collet assembly 50. The collet assembly 50 can include the collet members 430, the lock members 460, the biasing members 470 and a cover member 480. The collet member 430 has a distal end 462 and proximate end 463, and an inner surface 461 and an outer surface 464. In general, the retention mechanism 40 is located internally of the handpiece 30 and the collet assembly 50 is also located internally of the handpiece 30. In particular, the collet assembly 50 can be located in the passage 310 of the distal end 33 of the handpiece 30. The collet assembly 50 can be rotatably supported in the passage 310 for moving the locking members 460 between a first or locked (or coupled) position and a second or unlocked (or uncoupled) position. The collet assembly 50 can be biased toward the locked position by the biasing force of the biasing members 470.

Figure 7:
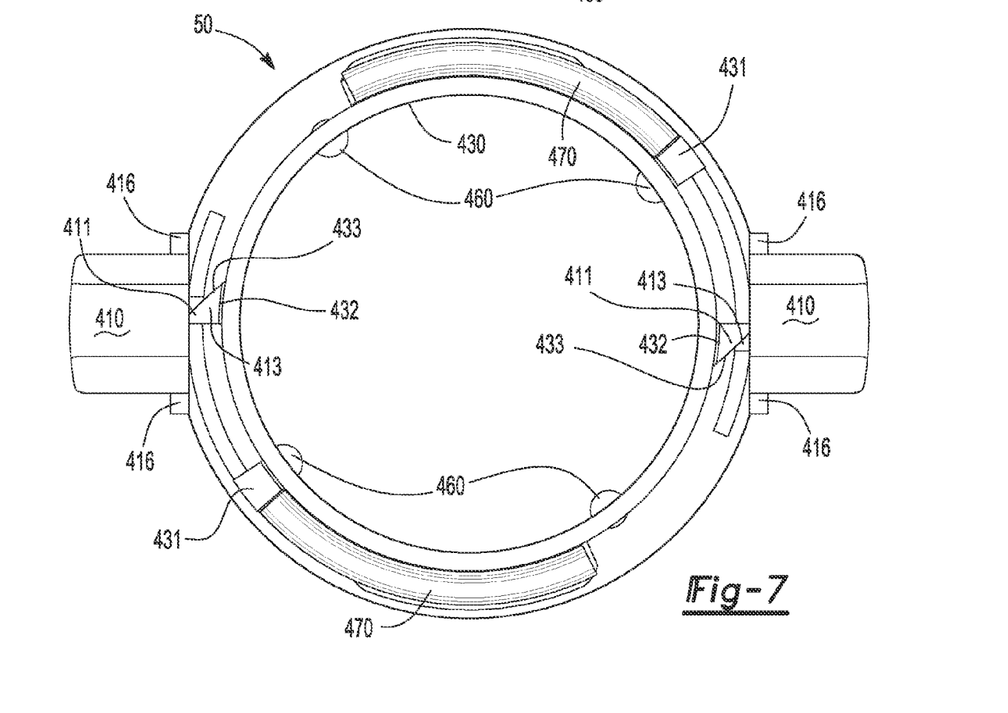
FIG. 7 is an end view of the collect member assembly of FIG. 6.
Figure 8:
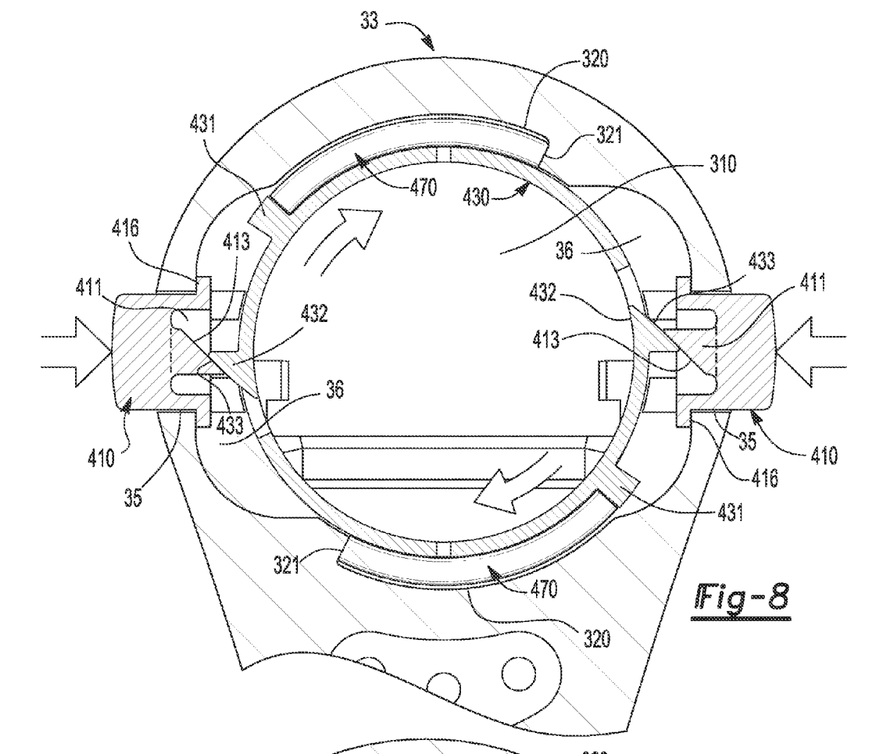
FIG. 8 is a sectional, end view of the blade retention mechanism and the surgical device in a first or locked position.
Figure 12:
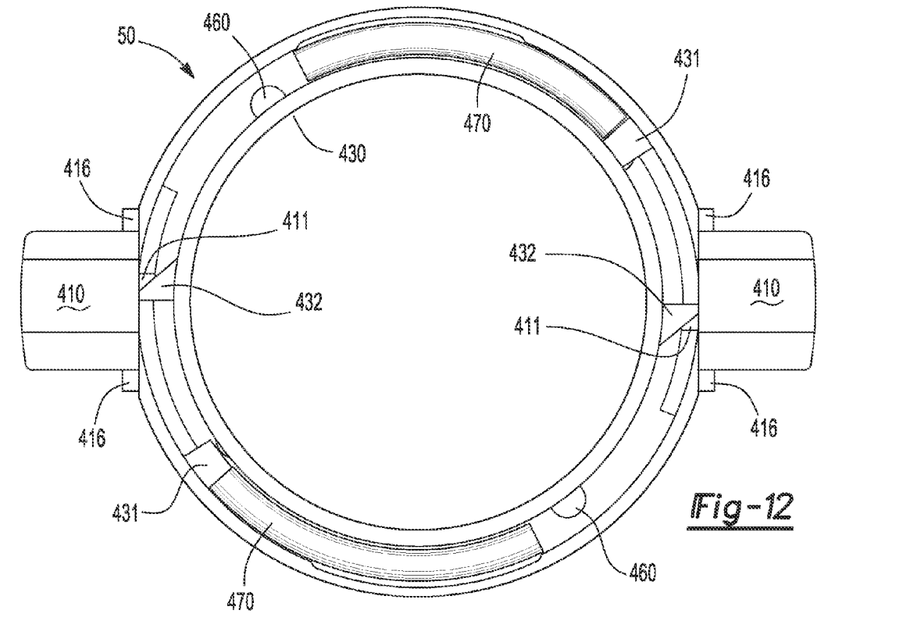
FIG. 12 is an end view of the collect member assembly of FIG. 11.

Since each radial passage 35 is in communication with the passage 310 in the distal end 33 of the handpiece 30, each movable button 410 can cause rotational movement of the collet assembly 50 which is rotatably supported in the passage 310 in the distal end 33 of the handpiece 30 against the biasing force of the biasing members 470. The collet member 430 of the collet assembly 50 is preferably a generally cylindrically-shaped member and is designed to fit within the passage 310 of the handpiece 30. The collet member 430 can include a pair of oppositely located radial extension members or tabs 431 which extend into a partial annular recess 320 of the passage 310. Each biasing member 470 can have one end in contact with the tab 431 and another end in contact with a wall 321 of the recess 320. The biasing member 470 is preferably a compression spring or similar compression biasing device disposed in the recess 320 in a compressed or biased state such that when the collect member 430 is installed there is an inherent biasing force present in the biasing member 470 causing the collet member to be biased toward the first or locked position—which is shown as being in the counter-clockwise direction FIG. 8 and in the clockwise direction in FIGS. 7 and 12.

The collet member 430 can also include a pair of oppositely disposed radially extending members or tabs 432 each of which includes a ramped or inclined surface 433 which can be angled to be substantially supplementary with the surface 413 of the button 410 as best shown in FIGS. 7-10 which show the collet assembly 50 in the first or locked position wherein the buttons 410 are at their radially extended limit in each radial passage 35 due to the biasing forces of the biasing members 470. However, unlike the ramped surfaces 413 of the buttons 410, each inclined surface 433 of each radial extension member 431 can be preferably arc-shaped and has a shallow angle of approximately about eight (8) degrees—equivalent to a very large radius as to generally appear to be linear or planar but functional to provide an operative amount of contact between with the ramped surface 413. Since the collet member 430 is substantially circular in cross-section, and the inclined surface 433 is not arranged perpendicular to the circular cross-section of the collet member 430, the inclined surface 433 of the first radial extension member 431 can define a chord of the first generally cylindrical passage 310.

The substantially supplementary ramped or inclined surfaces 413 and 433 can transfer rotational movement of the collet member 430 and the collet assembly 50 due to the biasing forces of the biasing members 470 to radially outward movement of each button 410 in the passage 35. Similarly, when a sufficient force is applied to move each button 410 radially inward in each passage 35 (i.e., a force sufficient to overcome the biasing forces of the biasing members 470), the substantially complementary ramped or inclined surfaces 413 and 433 can transfer the radially inward movement of the buttons 410 into rotational movement of the collet member 430 within the passage 310 to move the collet assembly 50 from the first or locked position, as shown in FIGS. 7-10, toward and to the second or unlocked position as shown in FIGS. 11-14. While the substantially supplementary ramped or inclined surfaces 413 and 433 are useful for transferring movement between the collet member 430 and the buttons 410, it should be understood that any known or later developed and appropriate interface can be used for transferring the movement of the two buttons 410 to the movement of the collet assembly 50 between the locked and unlocked positions. For example, it is contemplated that non-inclined surfaces may be used instead of the inclined surfaces 413 and 433 but will require a greater effort to actuate the collet assembly 50 in operation. Additional structures or devices may be used to then reduce the increased effort required to transfer the movement.

Figure 9:
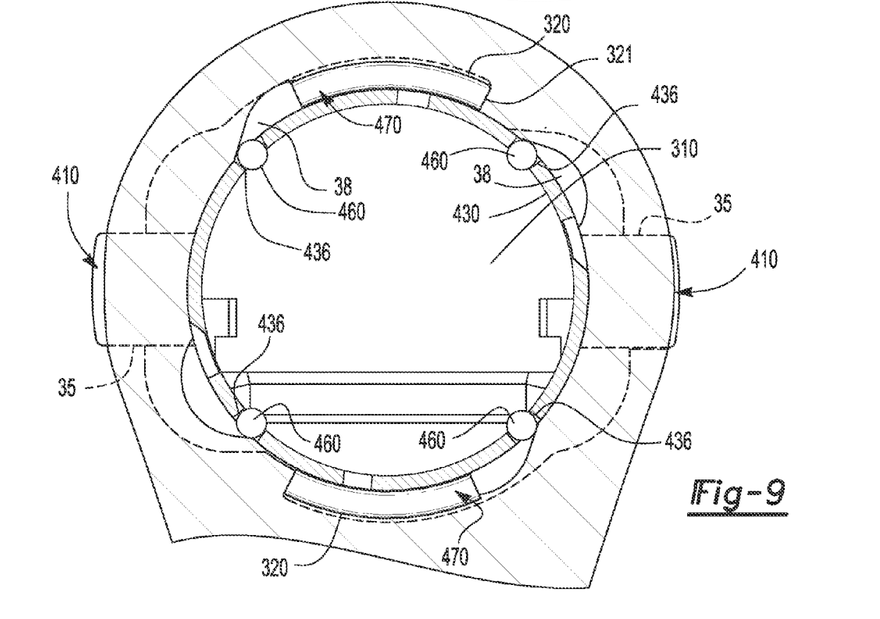
FIG. 9 is an alternate, sectional, end view of the blade retention mechanism and the surgical device in a first or locked position.
Figure 10:
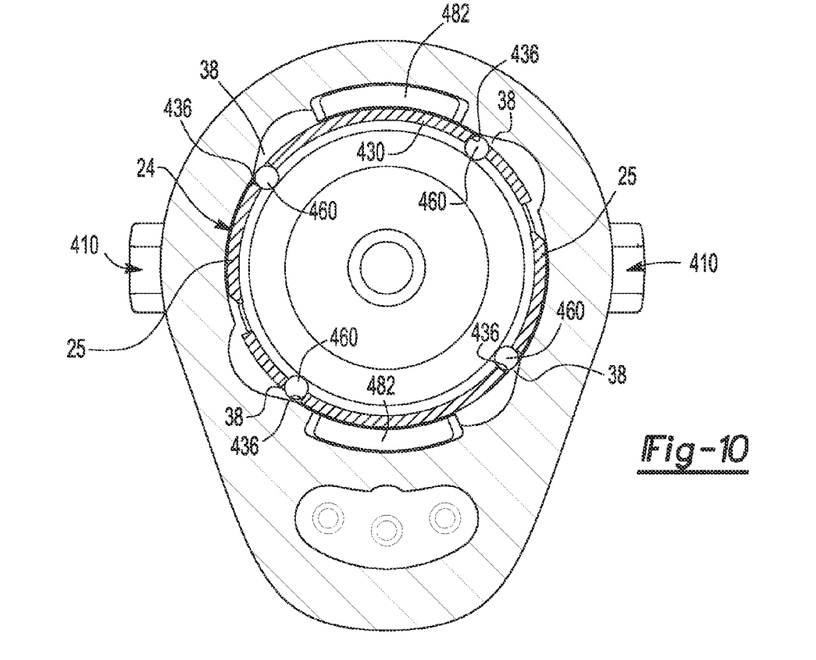
FIG. 10 is an alternate, sectional, end view of the blade retention mechanism and the surgical device, including the cutting blade, in a first or locked position.
Figure 11:
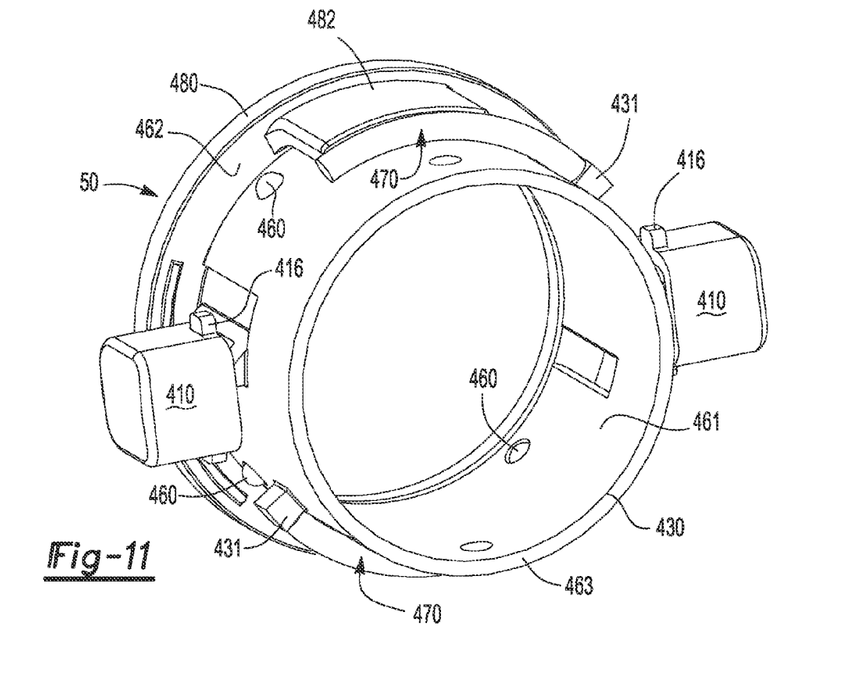
FIG. 11 is a perspective view of the collect member assembly of the handpiece of the blade retention mechanism of the surgical device in a second or unlocked position.
Figure 13:
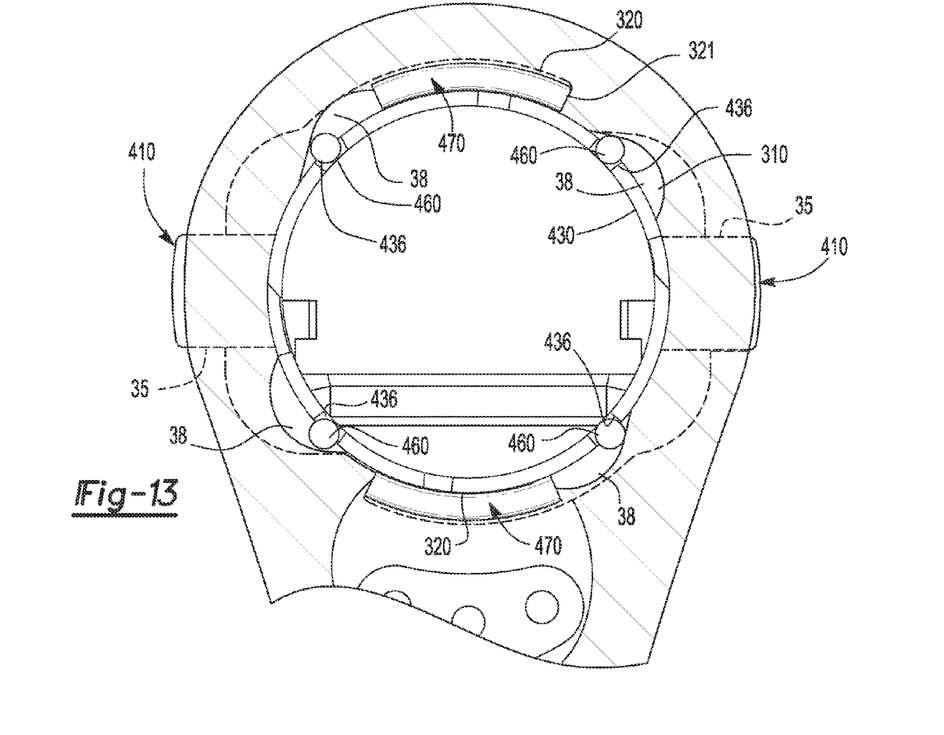
FIG. 13 is an alternate, sectional, end view of the blade retention mechanism and the surgical device in the second or unlocked position.
Figure 14:
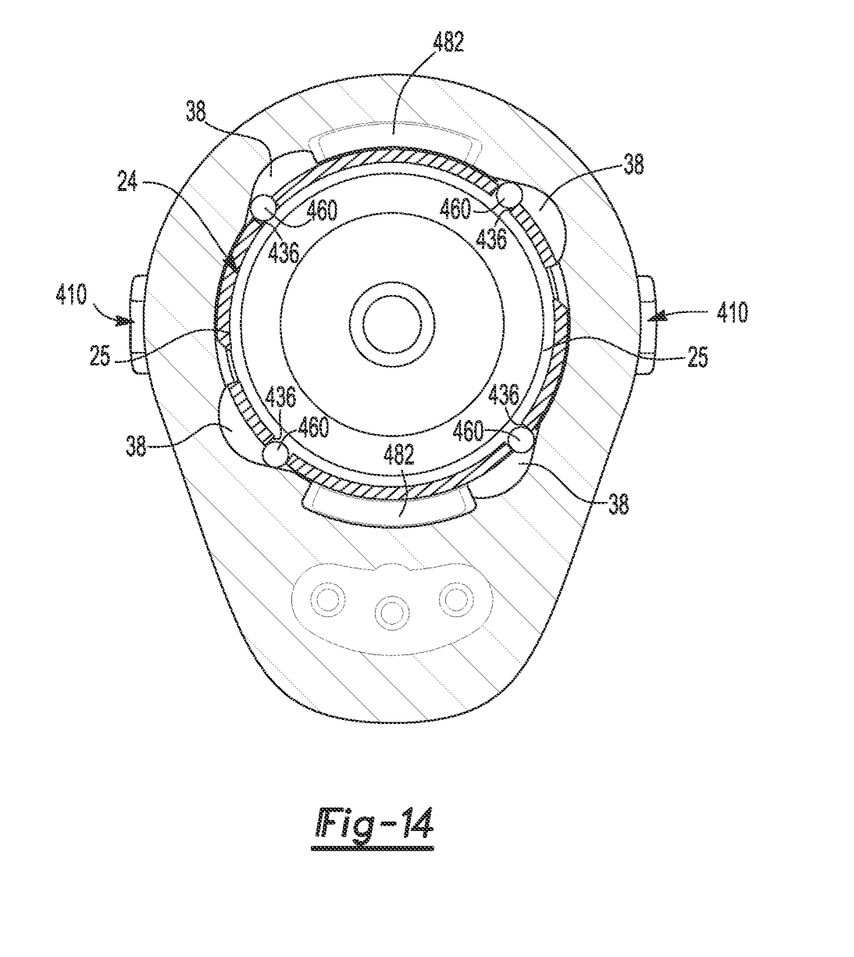
FIG. 14 is an alternate, sectional, end view of the blade retention mechanism and the surgical device, including the cutting blade, in the second or unlocked position.
Figure 15:
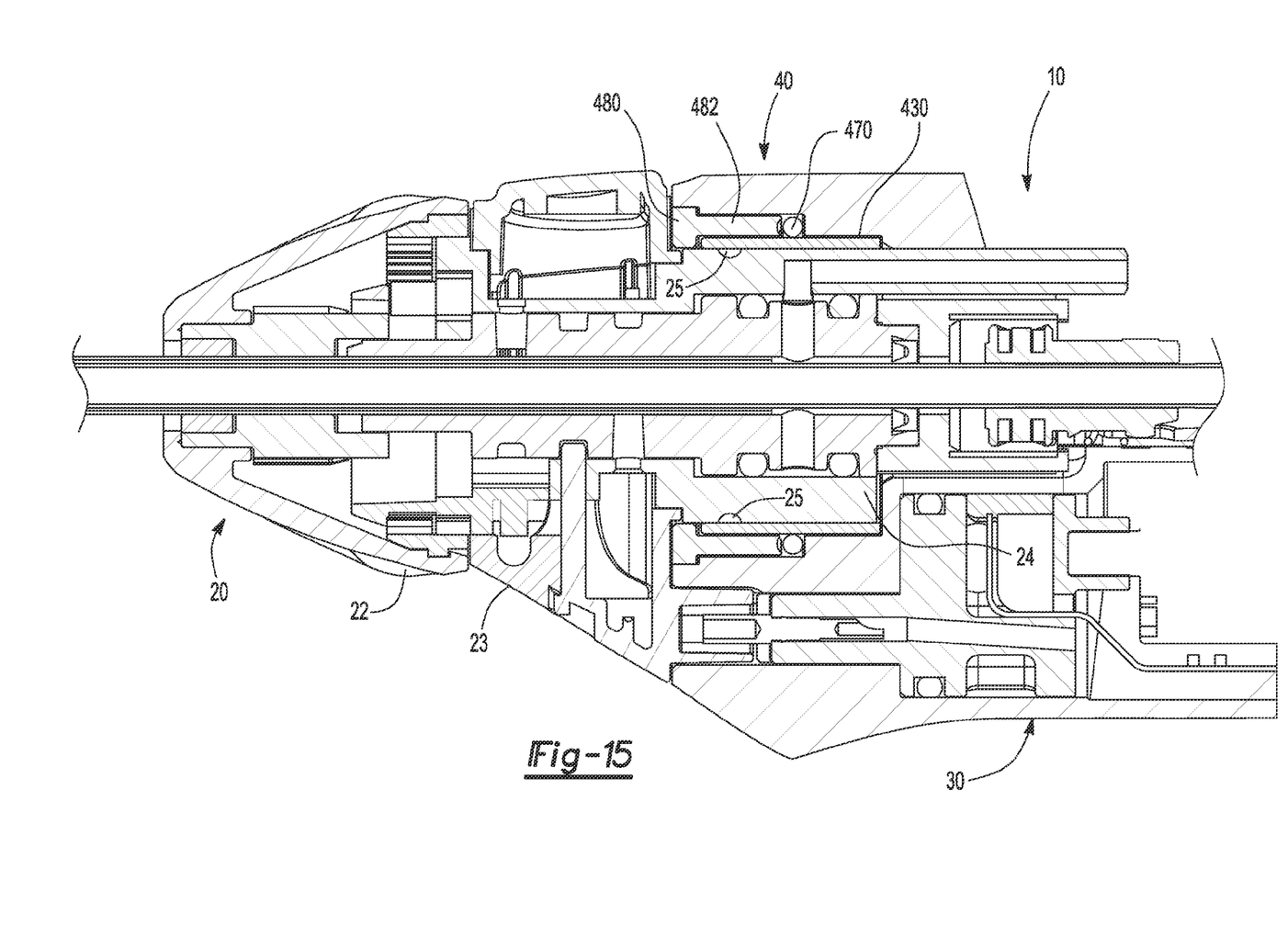
FIG. 15 is a longitudinal axis, cross sectional view of the blade retention mechanism and the surgical device, including the surgical tool cutting blade according to an exemplary embodiment of the present disclosure.

The collet assembly 50 can include a plurality of rolling lock members 460 which can be moved by the collet member 430 from a first or lock position, in which the lock members are forced by the wall of the passage to extend inwardly of the collet member 430 to engage the annular groove 25 of the surgical tool 20, and a second or unlocked position, in which the lock members 460 are aligned with a recess in the wall of the passage and are not forced to extend inwardly of the collet member 430. Each lock member 460 is generally a round, ball-shaped member having a diameter or first length. The collet member 430 can include a plurality of equally spaced radially extending holes 436, each of which can have associated therewith a lock member 460 as best shown in FIGS. 9 and 13. Each hole 436 can have a diameter at an inner surface of the collet member 430 that diameter of the hole 436 can have a second length wherein the second length of the hole 436 is less than the first length of the lock member 460 to limit the radially inward movement of the lock member 460 such that the lock member 460 is trapped between the surface of the passage 310 and the hole 436 of the collet member 430.

The retention mechanism 40 (nose portion) can further include a cover member 480 having a generally annular or disc shape and can include a pair of oppositely disposed axially extending tabs 482 having an arcuate extent portion for insertion in a recess in the passage 310. The cover member 480 can be located in the recess 311 in the distal end 33 of the handpiece 30 for retaining the collet assembly 50, at the distal end for the collet member 430, in the passage 310. The cover member 480 can be fixed to the distal end 33 of the handpiece 30 and can alternatively be removably fixed to allow service of the collet assembly. The inner edge of the disc portion of the cover member 480 can be aligned with the inner surface of the collet member 430 to provide a relatively continuous surface for receiving the end 24 of the surgical tool 20.

The passage 310 of the handpiece 30 can be further defined by a plurality of recesses 38 (channels) equally spaced apart and aligned slightly offset with a respective lock member 460 and a respective hole (passage) 436 of the collet member 430. When the collet member 430 is in the first or locked position, each lock member 460 can be offset to an end of each respective recess 38 such that each lock member 460 can engage the wall of the passage 310 and can be forced radially inwardly such that lock member 460 is relatively fixed in position can have at least a portion of the lock member 460 extending radially inward beyond the inner surface of the collet member 460 to engage the annular recess 25 of the end 24 of the surgical tool or device 20 to retain the surgical tool 20 in the handpiece 30. Actuation of the collet assembly 50 can rotate the collet member 430 which can move (i.e., rotate in either a clockwise or counter-clockwise direction) each lock member 460 toward each respective recess 38 in the passage 310 such that the wall of the passage 310 no longer can force the lock member radially inwardly to the second or unlocked (or uncoupled) position as shown in FIGS. 11-14. The recess 38 may be in the form of a radially and circumferentially extending channel of the main body 30. As noted herein, by pressing the buttons 410, the collet member 430 is rotated through the interaction of the inclined surfaces 413 and 433 against the biasing force of the biasing member 470.

Figure 16:
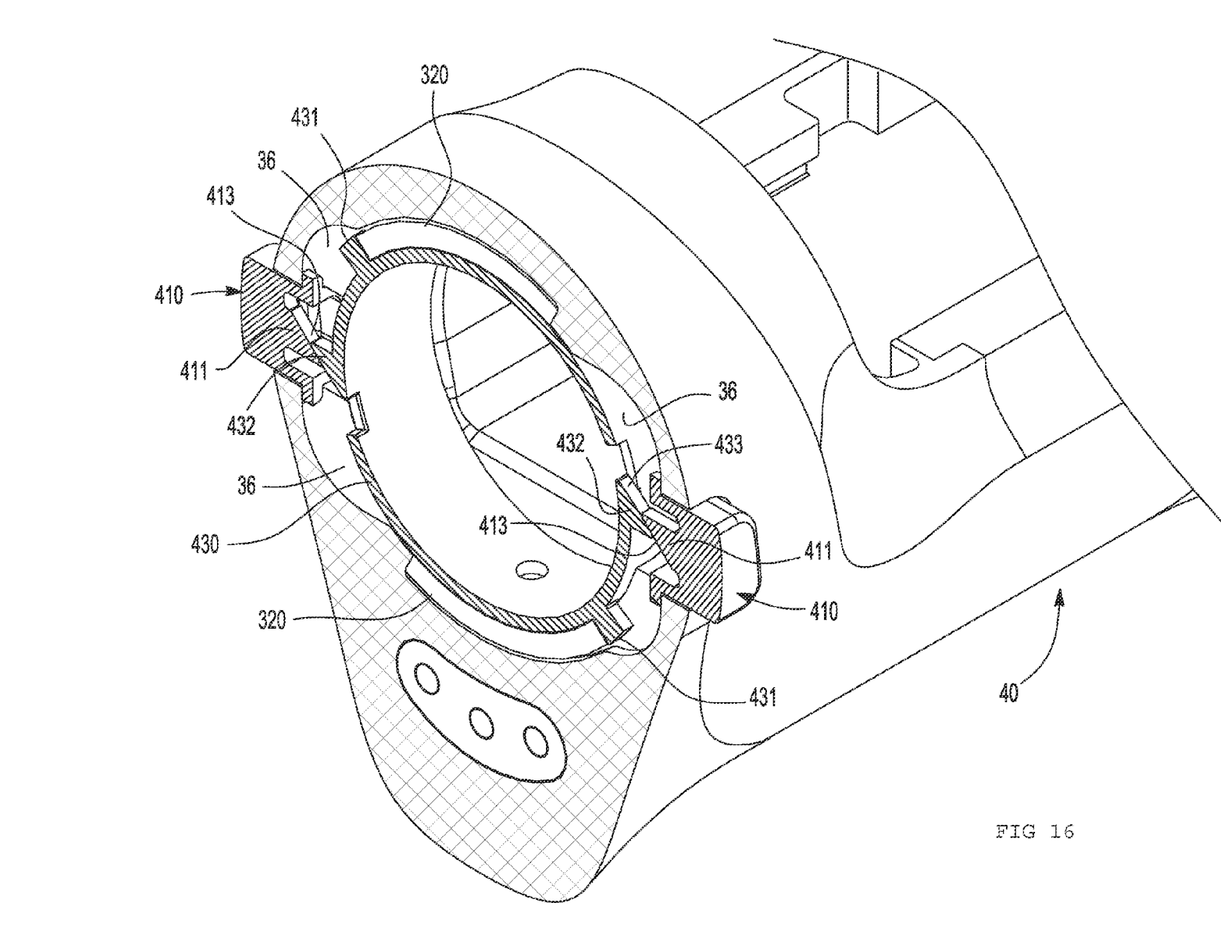
FIG. 16 is a cutaway view of the collet assembly in the blade retention assembly.

In practice, an operator of the surgical apparatus 10 can grip the handpiece 30 in any appropriate manner to present the distal end 33 and while gripping the surgical apparatus 10, also press the two buttons 410 to move the collet assembly 50 from the first or locked position to the second or unlocked position. With the collet assembly in the unlocked position, the operator may then insert the end 24 of the surgical tool 20 into the passage 310 in the distal end 33 of the handpiece 30 and release the buttons 410. Upon the release of the buttons 410, the biasing force of the biasing member 470, will cause the collet assembly 50 to move toward the first or locked position by rotate the collet member 430 which moves the lock members 460 toward the ends of the recesses 38 until the wall of the passage 310 moves the lock members radially inward in the holes 436 in the collet member 430. The force of the biasing members 470 can rotate the collet member 430 and thereby can force the each lock member 460 to move radially inwardly in each hole or passage 436 until the second length of each lock member 460 interferes with the length of its respective hole 436 and is locked in the first or lock position with a portion of the lock member 460 projecting into the annular recess 25 of the surgical tool. The portion of the lock member 460 projecting into the annular recess 25 can limit and/or prevent the surgical tool 20 from being removed from the handpiece 30. The surgical tool 20 will be retained by the retention mechanism 40 in the passage 310 in the handpiece 30 until the operator actuates the two buttons 410. FIG. 16 shows a cutaway view of the collet member 430 disposed in the blade retention mechanism wherein the cut away is through the axial moveable buttons located in the radially extending passage 35.

Any numerical values recited herein or in the figures are intended to include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the Detailed Description of the Invention of a range in terms of at "'x' parts by weight of the resulting polymeric blend composition" also contemplates a teaching of ranges of same recited amount of "x" in percent by weight of the resulting polymeric blend composition."

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein are intended to be open ended terms and also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The omission in the claims of any aspect of subject matter that is disclosed herein is not a disclaimer of such subject matter, nor should it be regarded that the inventors did not consider such subject matter to be part of the disclosed inventive subject matter.

The invention claimed is:

1. A surgical apparatus, comprising;
 a. a main body including;
  i. a first generally cylindrical passage having a proximal end and a distal end;
  ii. a second radially extending passage extending from the first generally cylindrical passage; and
  iii. a recess;
 b. a collet member supported for rotational movement in the first cylindrical passage of the main body, the collet member including:
  i. a first surface;
  ii. a passage having a first length; and
  iii. an inner surface;
 c. a biasing member biasing the collet member in a first rotational direction within the first generally cylindrical passage of the main body;
 d. a lack member having a second length, the lock member aligned in the passage of the collet member and extending radially inward beyond the inner surface of the collet member, the second length of the lock member being greater than the first length of the passage of the collet member wherein the collet member limits the lock member and retains the lock member within the first generally cylindrical passage of the main body; and
 e. an actuator radially movable in the second radially extending passage of the main body, the actuator including a second surface for engaging the first surface of the collet member wherein radially inward movement of the actuator against a force of the biasing member rotates the collet member within the first generally cylindrical passage and moves the lock member from a first locked position to a second unlocked position wherein the lock member can move radially outward to be at least partially located in the recess of the main body.

2. The surgical apparatus of claim 1 wherein the actuator comprises two buttons and the second radially extending passage of the main body comprises two radially extending portions located on opposite sides of the first generally cylindrical passage and wherein a button is located in each radially extending portion wherein radially inward movement of the two buttons rotates the collet member within the first generally cylindrical passage.

3. The surgical apparatus of claim 2 the lock member comprises a ball and the collet member includes a hole and wherein the ball moves radially in the hole when the surgical apparatus moves from the first locked position to the second unlocked position.

4. The surgical apparatus of claim 3 wherein the lock member comprises four equally spaced balls and the collet member includes four equally spaced holes.

5. The surgical apparatus of claim 2 further comprising a cover member aligned with the distal end of the collet member for securing the collet member in the passage of the main body.

6. The surgical apparatus of claim 2 further comprising a disc-shaped cover member aligned with the distal end of the collet member for covering the collet member and at least a portion of the distal end of the first generally cylindrical passage of the main body.

7. The surgical apparatus of claim 1 further comprising a disc-shaped cover member aligned with the distal end of the collet member for covering the collet member and at least a portion of the distal end of the first generally cylindrical passage of the main body.

8. The surgical apparatus of claim 7 wherein the disc-shaped cover member includes first and second tabs each extending in a direction aligned with an axis of the first generally cylindrical passage of the main body and wherein the first and second tabs are oppositely spaced.

9. The surgical apparatus of claim 1 further comprising a cover member aligned with the distal end of the collet member for covering the collet member and at least a portion of the distal end of the first generally cylindrical passage of the main body.

10. A surgical apparatus, comprising:
   a. a main body including a nose portion for selectively coupling a disposable surgical instrument to the surgical apparatus, the nose portion including:
       i. a first generally cylindrical passage having a proximal end and a distal end;
       ii. a second radially extending passage extending from the first generally cylindrical passage; and
       iii. a radially and circumferentially extending channel;
   b. a collet member having a proximal end and a distal end, the collet member supported for rotational movement in the first generally cylindrical passage of the nose portion, the collet member including:
       i. a first radially extending member including a first surface;
       ii a second radially extending member including a second surface extending substantially perpendicular to an outer surface of the collet member;
       iii. a passage having a first length; and
       iv. an inner surface
   c. a biasing member having a first end and a second end, the biasing member located in the first generally cylindrical passage and biasing the collet member in a first rotational direction;
   d. a lock member having a second length, the lock member aligned in the passage of the collet member and extending radially inward beyond the inner surface of the collet member, the second length of the lock member being greater than the first length of the passage of the collet member wherein the collet member limits the lock member and retains the lock member within the first generally cylindrical passage of the main body; and
   e. a first actuator radially movable in the second radially extending passage of the main body, the first actuator including a second surface for engaging the first surface of the first radially extending member of the collet member wherein radially inward movement of the first actuator against a force of the biasing member rotates the collet member within the first generally cylindrical passage and moves the lock member from a first locked position to a second unlocked position wherein the lock member is at least partially located in the radially and circumferentially extending channel of the main body.

11. The surgical apparatus of claim 10 further comprising a cover member aligned with the distal end of the collet member for securing the collet member in the passage of the main body.

12. The surgical apparatus of claim 11 wherein the cover member includes first and second tabs each extending in a direction aligned with an axis of the first generally cylindrical passage of the main body and wherein the first and second tabs are oppositely spaced.

13. The surgical apparatus of claim 10 further comprising a disc-shaped cover member aligned with the distal end of the collet member for covering the collet member and at least a portion of the distal end of the first generally cylindrical passage of the main body.

14. The surgical apparatus of claim 10 wherein
   a. the main body further includes a third radially extending passage located opposite the first radially extending passage and
   b. the collet member further includes a second radially extending member including a third surface, the second radially extending member located opposite the first radially extending member; and
   c. the surgical apparatus further comprising;
       i. a second actuator radially movable in the third radially extending passage of the main body, the second actuator including a second surface for engaging the third surface of the second radially extending member of the collet member wherein radially inward movement of both the first actuator and the second actuators against the force of the biasing member rotates the collet member within the first generally cylindrical passage and moves the lock member from the first locked position to the second unlocked position.

* * * * *